US012558490B2

(12) United States Patent
Bohling et al.

(10) Patent No.: US 12,558,490 B2
(45) Date of Patent: Feb. 24, 2026

(54) APPARATUS FOR DETECTING A MANIPULATION OF AN INJECTION DEVICE

(71) Applicant: Sanofi, Paris (FR)

(72) Inventors: Stefan Bohling, Frankfurt am Main (DE); Michael Jugl, Frankfurt am Main (DE); Stephan Mueller-Pathle, Frankfurt am Main (DE)

(73) Assignee: SANOFI, Paris (FR)

( * ) Notice: Subject to any disclaimer, the term of this patent is extended or adjusted under 35 U.S.C. 154(b) by 871 days.

(21) Appl. No.: 17/787,664

(22) PCT Filed: Dec. 22, 2020

(86) PCT No.: PCT/EP2020/087610
§ 371 (c)(1),
(2) Date: Jun. 21, 2022

(87) PCT Pub. No.: WO2021/130216
PCT Pub. Date: Jul. 1, 2021

(65) Prior Publication Data
US 2022/0409819 A1      Dec. 29, 2022

(30) Foreign Application Priority Data
Dec. 27, 2019    (EP) .................................... 19306777

(51) Int. Cl.
*A61M 5/315*          (2006.01)
(52) U.S. Cl.
CPC .... *A61M 5/31568* (2013.01); *A61M 5/31551* (2013.01); *A61M 2205/50* (2013.01);
(Continued)
(58) Field of Classification Search
CPC ...................... A61M 5/31551; A61M 5/31568
See application file for complete search history.

(56) References Cited

U.S. PATENT DOCUMENTS

| | | | |
|---|---|---|---|
| 6,277,099 B1 | 8/2001 | Strowe et al. | |
| 7,935,088 B2 | 5/2011 | Veasey et al. | |

(Continued)

FOREIGN PATENT DOCUMENTS

| | | |
|---|---|---|
| JP | 2001087386 A | 4/2001 |
| JP | 2012515587 A | 7/2012 |

(Continued)

OTHER PUBLICATIONS

International Preliminary Report on Patentability in International Appln. No. PCT/EP2020/087610, mailed on Jul. 7, 2022, 10 pages.

(Continued)

*Primary Examiner* — Deanna K Hall
(74) *Attorney, Agent, or Firm* — Bond, Schoeneck & King, PLLC

(57)          ABSTRACT

An apparatus configured to be arranged within a housing of an injection device and for detecting a manipulation of the injection device comprises a cam part that is configured to be rotatable relative to a follower part; a resilient member arranged to urge the cam part and the follower part towards abutment with each other wherein rotation of the cam part relative to the follower part causes reciprocating motion of the follower part, wherein the follower part is configured to move reciprocally in an axial direction of the injection device; and a contact sensor provided between the cam part and the follower part and configured to detect the reciprocating motion of the follower part. The cam part comprises a profiled section comprising an axially varying profile arranged to be in abutment with the follower part and configured to cause reciprocating motion of the follower part.

20 Claims, 6 Drawing Sheets

(52) U.S. Cl.
CPC ................. *A61M 2205/581* (2013.01); *A61M 2205/8212* (2013.01)

(56) References Cited

U.S. PATENT DOCUMENTS

| | | |
|---|---|---|
| 2013/0296802 A1 | 11/2013 | Moore et al. |
| 2019/0022328 A1 | 1/2019 | Schleicher et al. |

FOREIGN PATENT DOCUMENTS

| | | | | |
|---|---|---|---|---|
| JP | 2020528799 A | 10/2020 | | |
| JP | 2020529878 A | 10/2020 | | |
| WO | WO 2004/078241 | 9/2004 | | |
| WO | WO 2019/040313 | 2/2019 | | |
| WO | WO-2019040313 A1 * | 2/2019 | ............. | A61M 5/20 |
| WO | 2019046053 A1 | 3/2019 | | |
| WO | WO 2019/121616 | 6/2019 | | |

OTHER PUBLICATIONS

International Search Report and Written Opinion in International Appln. No. PCT/EP2020/087610, mailed on Mar. 16, 2021, 12 pages.

Needle-based injection systems for medical use Requirements and test methods, Part 1: Needle injection systems, ISO 11608-1:2014(E), Third Edition, Switzerland, ISO, Dec. 15, 2014, pp. 1-13.

Notice of Reasons for Refusal, JP Patent Application No. 2022-539142, dated Oct. 1, 2024, pp. 1-6 (with pp. 1-3 being a translation).

Search Report, JP Patent Application No. 2022-539142, dated Sep. 13, 2024, pp. 1-23 (with pp. 1-13 being a translation).

Decision to Grant, JP Patent Application No. 2022-539142, dated Feb. 4, 2025, pp. 1-5 (with pp. 1-2 being a translation).

* cited by examiner

APPARATUS FOR DETECTING A MANIPULATION OF AN INJECTION DEVICE

CROSS REFERENCE TO RELATED APPLICATIONS

The present application is the national stage entry of International Patent Application No. PCT/EP2020/087610, filed on Dec. 22, 2020, and claims priority to Application No. EP 19306777.4, filed on Dec. 27, 2019, the disclosures of which are incorporated herein by reference.

TECHNICAL FIELD

The present disclosure relates to an apparatus for detecting a manipulation of an injection device and in particular to an apparatus for detecting a manipulation of a dose setting or a dose dispensing mechanism of the injection device during injection of a medicament.

BACKGROUND

A variety of diseases exists that require regular treatment by injection of a medicament. Typically a medical practitioner formulates a dosage regime that manages the timing and dosage of the injections a patient should follow. Thus the timing and/or the dosage of the injections can vary between patients and between injections. Often, as part of the dosage management regime, users are required to record parameters of the injections, for example to monitor effectiveness of the treatment or as feedback during the calculation of parameters for subsequent injections. This could be achieved through the keeping of a manual data logbook.

The injections can be performed either by medical personnel or by patients themselves by using injection devices. Injection devices (i.e. devices capable of delivering medicaments from a medication container) typically have a syringe connected to a medicament container and a dose dispensing mechanism for driving the medicament through the needle. The medicament chamber may be re-useable wherein the dose dispensing mechanism is designed to be reset, allowing an empty medicament cartridge to be replaced by a new one. Alternatively, the injection device may be disposable wherein, upon the contents of a pre-filled medicament container being emptied, the injection device is disposed of. Suitably, the injection device includes a dose setting mechanism that allows a user to set or 'dial in' an amount of medicament to be administered.

As an example, type-1 and type-2 diabetes can be treated by patients themselves by injection of insulin doses according to a dosage regime, for example injections once or several times per day. WO2004/078241 discloses a suitable injection device typically referred to as a pen and references to pen herein are interchangeable with injection device. It is known for a disposable pen to be provided with a set of one-way needles that are attached to the pen before each use. The insulin dose to be injected and prescribed by the dosage regime can then, for instance, be manually selected through the dose setting mechanism by turning a dose knob to the required volume. The dose is then injected by inserting the needle into a suited skin portion and pressing an injection button of the dose dispensing mechanism. As part of the management of the dosage regime, the user records parameters of the injection. Such parameters, for instance, may be one or more of; the date and time of injection, blood sugar results, medication and dose, and/or diet and exercise information.

SUMMARY

According to various aspects of the present specification, there is provided an apparatus for detecting a manipulation of an injection device, the apparatus comprising: a cam part that is configured to be rotatable relative to a follower part; a resilient member arranged to urge the parts towards abutment with each other wherein rotation of the cam part relative to the follower part causes reciprocating motion of the follower part; and a contact sensor provided between the cam part and the follower part and configured to detect the reciprocating motion of the follower part.

According to various aspects of the present specification there is provided an apparatus configured to be arranged within a housing of an injection device and for detecting a manipulation of the injection device, the apparatus comprising:

- a cam part that is configured to be rotatable relative to a follower part;
- a resilient member arranged to urge the parts towards abutment with each other wherein rotation of the cam part relative to the follower part causes reciprocating motion of the follower part, wherein the follower part is configured to move reciprocally in an axial direction of the injection device; and
- a contact sensor provided between the cam part and the follower part and configured to detect the reciprocating motion of the follower part,
- wherein the cam part comprises a profiled section comprising an axially varying profile arranged to be in abutment with the follower part and configured to cause reciprocating motion of the follower part, and
- wherein the contact sensor is arranged on the cam part and is configured to separate from the follower part upon reciprocal movement of the follower part.

By providing a contact sensor between the cam part and the follower part, the contact sensor can provide a signal in response to the reciprocating motion of the follower part. The signal can be used to determine a dose delivered by the injection device, or a dose dialed into the injection device, from the detected reciprocating motion of the follower part.

According to the exemplary embodiments, there is therefore provided an improved injection device as set forth in the appended claims. Other features of the present disclosure will become apparent from the description and elsewhere in the application. By using a sensor to monitor the movement of a part of the injection device, a dose measurement can be electronically recorded, thus providing improved dose management ability.

BRIEF DESCRIPTION OF THE FIGURES

Exemplary embodiments are described with reference to the accompanying drawings, in which.

Reference will now be made in detail to exemplary embodiments, examples of which are illustrated in the accompanying drawings, wherein like reference numerals refer to like elements throughout.

DETAILED DESCRIPTION

Figure 1:
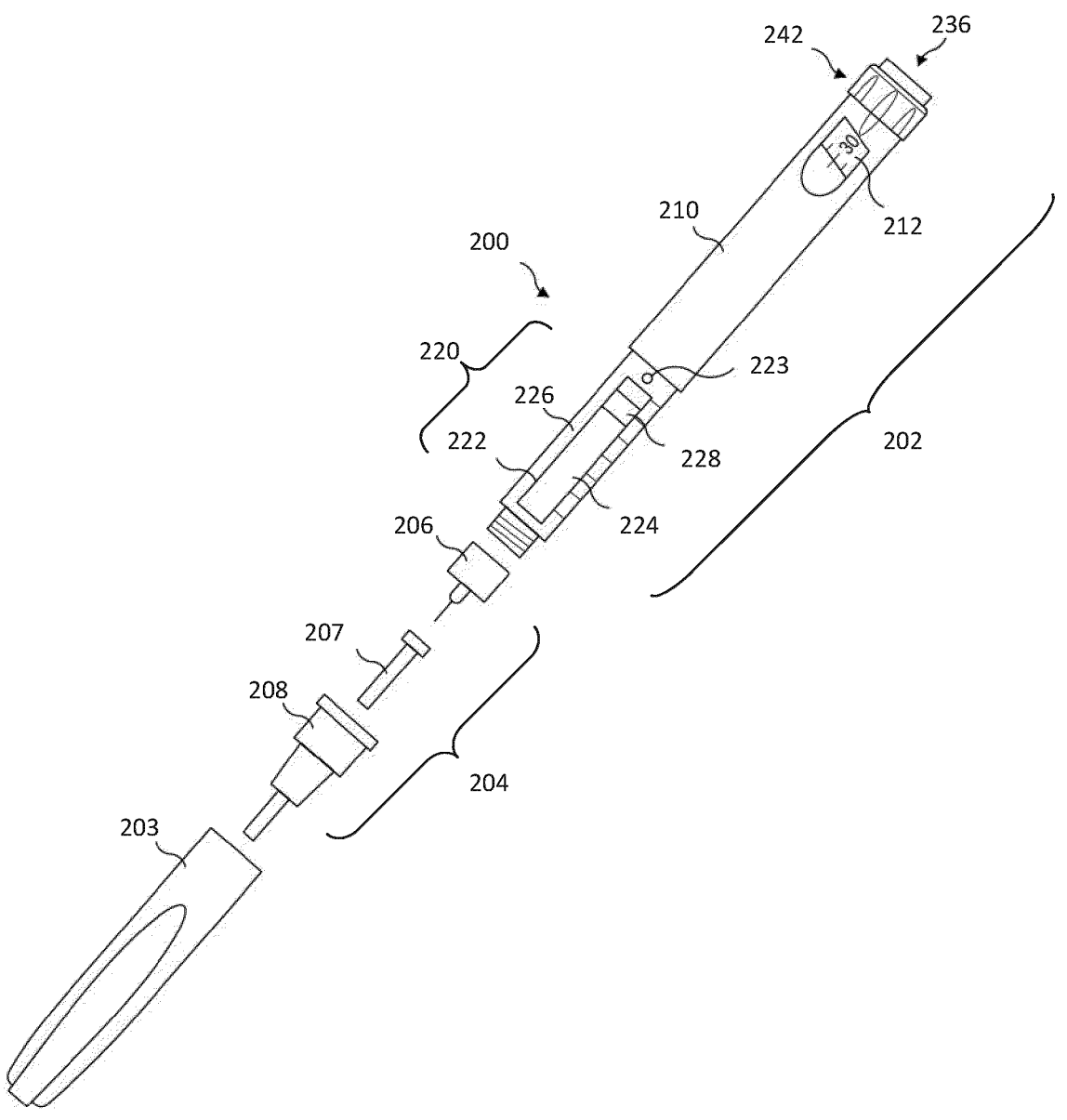
FIG. 1 shows a schematic view of an injection device.

FIG. 1 is an exploded view of an injection device 200 suitable for use with exemplary embodiments. The injection device shown is often referred to as an injection pen or pen. Various designs of pen are known and whilst a brief description is given herein, it will be appreciated that the specific construction of the pen may alter and vary from the following description.

The injection device 200 has a distal end and a proximal end. The term "distal" refers to a location that is relatively closer to a site of injection, and the term "proximal" refers to a location that is relatively further away from the injection site.

The injection device 200 comprises a grip assembly 202, a cap 203 and a needle assembly 204. The grip assembly is formed from a housing 210 and a cartridge assembly 220. The cartridge assembly 220 includes a cartridge holder 222 for containing a cartridge 224 containing medicament. As shown, housing 210 is substantially cylindrical and has a substantially constant diameter along its longitudinal axis from a proximal end to a distal end. The longitudinal axis has a proximal-distal direction that extends from the proximal end to the distal end and the reverse distal-proximal direction.

The cartridge assembly 220 is assembled to the housing 210 to form the grip assembly 202. Suitably, the proximal end of the cartridge assembly 220 includes a connection part (not shown) and the distal end of the housing 210 includes a corresponding connection part (not shown) that cooperatively engage with each other to connect the two parts. As shown, the cartridge holder 222 is substantially cylindrical with a hollow receiving for the cartridge 224. The cartridge includes a stopper 228 that can be advanced within the cartridge 224 during use to expel medicament from the cartridge 224. Here, it will be appreciated that the needle assembly 204 cooperates with the grip assembly to serve as a conduit for the medicament during injection.

The cartridge holder 222 has a porthole 226 in a side thereof. The porthole 226 allows the user to view the cartridge 224 through the porthole 226 when the cartridge 224 is contained in the cartridge holder 222. FIG. 1 shows a stopper 228 of the cartridge 224 visible through the porthole 226. FIG. 1 shows the cartridge holder 222 having one porthole 226, however, the cartridge holder 222 may instead have more than one porthole 226. For example, the cartridge holder 222 may have a first porthole 226 located on one side of the cartridge holder 222 and a second porthole located on a second, in some cases opposing, side of the cartridge holder 222. Thus a first side of the cartridge 224 within the cartridge holder 222 may be visible through the first porthole 226 while a second, different side of the cartridge 224 may be visible through the second porthole. Other porthole configurations may be used.

The needle assembly is shown comprising a needle 206, an inner needle cap 207 and an outer needle cap 208. A needle 206 of the needle assembly 204 can be affixed to the cartridge holder 222 such that the needle 206 is in fluid communication with the medicament in the cartridge 224. The needle 206 is protected by the inner needle cap 207 and the outer needle cap 208, The removable cap 203 attaches to the cartridge assembly. The cap 203 at least partially covers the cartridge holder 222, and hence cartridge 224, when attached to the grip assembly. The cap 203 may also be attached to the grip assembly such that it at least partially covers the cartridge holder 222 with or without one or more of the needle 206, inner needle cap 207 or outer needle cap 208 being present.

The cartridge holder 222 may have a cap retaining feature 223 on an outer surface, for example adjacent a proximal end of the cartridge holder 222, and adjacent the attachment to the housing 210. Thus, the cap 203 may substantially cover the cartridge assembly when fitted. The cap retaining feature 223 engages with a corresponding coupling feature on an inner surface of the cap 203 to hold the cap 203 in place when attached to the grip assembly. The cap retaining feature 223 may comprise one or more of a ridge, groove, bump, lock and/or pip. In some examples, the cap retaining feature is located on the housing 210 of the injection device 200.

Figure 2:
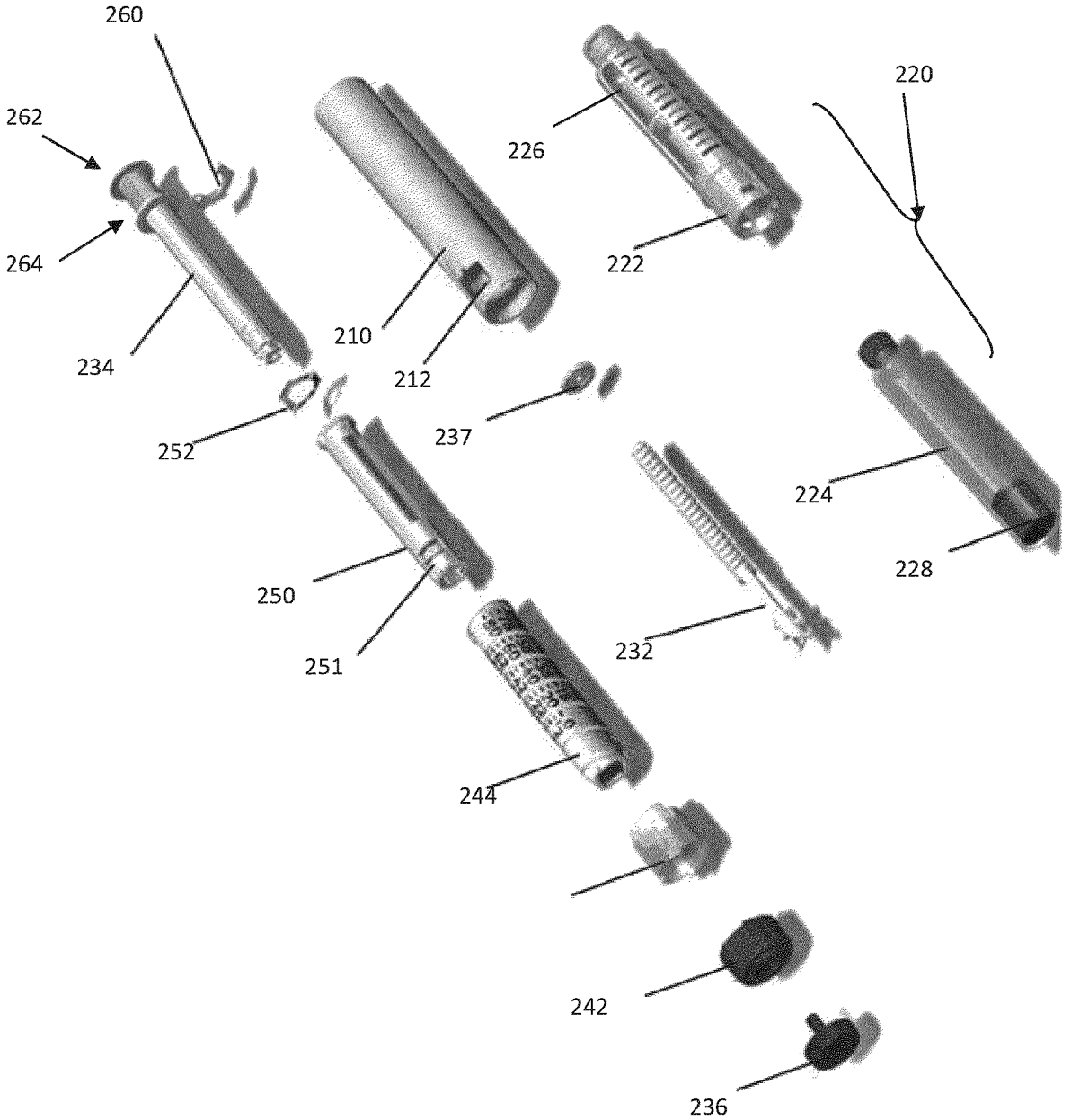
FIG. 2 shows an exploded parts view of the injection device of FIG. 1.

As shown in FIG. 2, the housing 210 houses a dose dispensing mechanism and a dose selection mechanism. The dose setting mechanism is used to select a dose to be injected and the dose dispensing mechanism is activated to inject the dose. In this instance, the dose dispensing mechanism is activated to drive the stopper 228 towards the distal end of the cartridge 224. The injection device 200 may be used for several injection processes until either the cartridge is empty or the expiration date of the injection device 200 (e.g. 28 days after the first use) is reached. Injection device 200 may be single-use or reusable.

To drive the stopper 228 into the cartridge 224, the dose dispensing mechanism includes a piston rod 232, a drive sleeve 234, and a trigger button 236, which act together to drive a pressure plate 237 against the stopper 228 and into the cartridge 224. A medicament or drug dose to be ejected from the drug delivery device 200 is selected by turning a dosage knob 242, which is connected by a threaded insert 243 to a dose dial sleeve 244, where rotation of the dose dial sleeve 244 by the dosage knob 242 causes the selected dose to be displayed in a dosage window 212 in the housing 210 and causes a clicker 250 to interact with the drive sleeve 234 via a spring clutch 252. Together, the dosage knob 203, dose dial sleeve 230, and clicker 250 are a dose setting mechanism. The dose dial sleeve 244 is arranged around the clicker 250, which includes a feedback mechanism 251 that generates a tactile or audible feedback with rotation of the dose dial sleeve 244. The clicker 250 is coupled to the drive sleeve 234 with a metal clutch spring 252.

A last dose nut 260 (LDN) is provided on the drive sleeve 234. The last dose nut 260 advances with each dose dispensing operation to track the total medicament remaining in the cartridge 224. The trigger button 236 is depressed to activate a dose dispensing operation of the drug delivery device 200. The drive sleeve 234 includes flanges 262 and 264 that project from the drive sleeve. For instance, the flanges may be radial flanges. The LDN 260 is a threaded part, and suitably a half nut. The drive sleeve includes a threaded bolt section that typically extends between the two flanges. As the drive sleeve is rotated by corresponding rotation of the dose setting mechanism, the LDN 260 is caused to move along the drive sleeve by cooperation of the respective threads. The LDN is suitably arranged to move from flange 262, which is a minimum flange indicating the starting position of the LDN when the LDN abuts the flange and the cartridge is full. The LDN iteratively moves along the drive sleeve as each dose is injected. The LDN advances in response to rotation of the dose setting mechanism but does not translate relative to the drive sleeve as the drive sleeve is driven during the dose dispensing operation. The LDN abuts the other flange, which is a maximum flange that prevents the LDN from moving and consequently prevents the dose dialed mechanism from dialing in a dose that would exceed the dose remaining in the cartridge.

While the dose setting mechanism is illustrated as the dosage knob 242, dose dial sleeve 244, and the clicker 250, as described above, one skilled in the art will appreciate that any number of different dose setting mechanisms that are routine in the art for the purposes of setting a dose of a drug delivery device and aspects of the present disclosure are compatible with other such dose setting mechanisms. Similarly, while the dose dispensing mechanism is illustrated as including the piston rod 232, drive sleeve 234, trigger button 236, one skilled in the art will appreciate that a number of different dose dispensing mechanisms (e.g., drive mechanisms) are known in the art for the purposes of delivering or dispensing a dose of a drug delivery device and aspects of the present disclosure are compatible with other such dose dispensing mechanisms.

Continuing with the operation of the drug delivery device 200, turning the dosage knob 236 causes a mechanical click sound to provide acoustic feedback to a user by rotating the dose dial sleeve 244 with respect to the clicker 250. The numbers displayed in the dosage display 212 are printed on the dose dial sleeve 244 that is contained in the housing 210 and mechanically interacts with the drive sleeve 234 via the metal spring clutch 252. When the injection button 236 is pushed, the drug dose displayed in the display 212 will be ejected from the drug delivery device 100. During a dose setting operation, the drive sleeve 234 is helically rotated with the dose dial sleeve 234 spiraling outwardly in the distal-proximal direction. When the injection button 236 is pushed, the drive sleeve 234 is released and advanced distally, which causes rotation of the piston rod 232. The rotation of the piston rod 232 drives the pressure plate 237 against the stopper 228 of the cartridge 224, which drives the stopper 228 into the cartridge 224 to expel the medicament from the cartridge 224. A more detailed description of a representative drug delivery device is described in U.S. Pat. No. 7,935,088 B2, issued 3 May 2011.

FIG. 2 shows the drug delivery device 200 at the end of a dose setting operation and prior to a dose dispensing operation, where the dose dial sleeve 244 and the drive sleeve 234 have been helically rotated with respect to the housing 210 and a threaded end 233 of the piston rod 232 to set the dose. The last dose nut 260 is shown advanced along the drive sleeve 234 from an initial position to a position indicative of the dose remaining in the drug delivery device 200. Upon dose dispensing of the injection button 236, the drive sleeve 234 advances into the housing 210 and a bearing nut 280 induces rotation of the piston rod 232. The bearing nut 280 sits fixed inside the housing 210 and has a threaded engagement with the piston rod 232. As the piston rod 232 rotates, the piston rod 232 is screwed forward (relative to the housing 210) because the bearing nut 280 cannot move. The rotation of the piston rod 232 drives the piston rod 232 and the pressure plate 237 proximally in the proximal-distal direction to drive the stopper 228 into the cartridge 224. Once dispensed, the drive sleeve is in a non-dose dialed position.

A medicament dose to be ejected from injection device 200 can be selected by turning the dosage knob 242, and the selected dose is then displayed via dosage window 212, for instance in multiples of International Units (IU). An example of a selected dose displayed in dosage window 12 may be '30' IUs, as shown in FIG. 1. It should be noted that the selected dose may equally well be displayed differently, for instance by means of an electronic display.

Turning the dosage knob 242 causes a mechanical click sound to provide acoustic feedback to a user. The numbers displayed in dosage window 212 are printed on the sleeve 244 that is contained in housing 210. When needle 206 is stuck into a skin portion of a patient, and then injection button 236 is pushed, the medicament dose displayed in display window 212 is ejected from injection device 200. When the needle 206 of injection device 200 remains for a certain time in the skin portion after the injection button 236 is pushed, a high percentage of the dose is actually injected into the patient's body. Ejection of the medicament dose also causes a dispensing clicker to provide a mechanical click sound, which is however different from the sounds produced by the clicker 250 when using dosage knob.

Whilst a pen injection device is briefly described, other injection devices are envisaged, as is known in the art.

Figure 3:
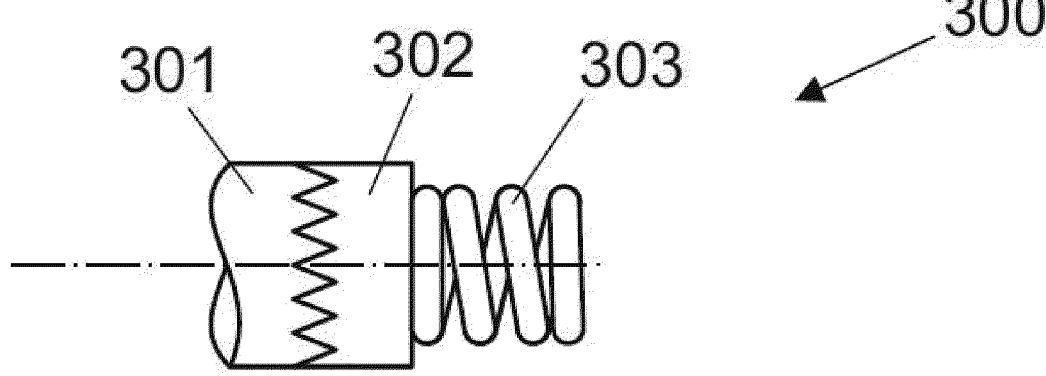
FIG. 3 shows a cross section view of a dosage counting mechanism.

FIG. 3 shows a dispensing clicker 300 comprising a cam part 301, a follower part 302 and a spring 303. The spring 303 is arranged to urge the follower part 302 against the cam part 301. The cam part 301 is attached to the housing 210.

In some examples, the follower part 302 may be coupled to the dose dispensing mechanism. For instance, the follower part 302 may be attached to the piston rod 232. In such examples, the dispensing clicker 300 may be configured to detect a dispensed dose.

In some other examples, the follower part 302 may be coupled to the dose setting mechanism. In such examples, the dispensing clicker 300 may be configured to detect the set dose.

The cam part 301 is configured to be fixed relative to the follower part 302. The cam part 301 is constrained from moving axially. The follower part 302 is moveable axially by compression and extension of the spring 303. The follower part 302 is configured to rotate as the dose is being delivered during the delivery phase.

The cam part 301 comprises a profiled section, shown as a sawtooth profile in the Figure. The follower part 302 has a corresponding profile, configured to engage with the profiled part of the cam part 301. The profiled sections of the cam part 301 and the follower part 302 are fully engaged in the Figure. The spring 303 is arranged to urge the follower part 302 against the cam part 301. The spring 303 maintains the engagement between the profiled sections of the cam part 301 and the follower part 302.

Figure 4:
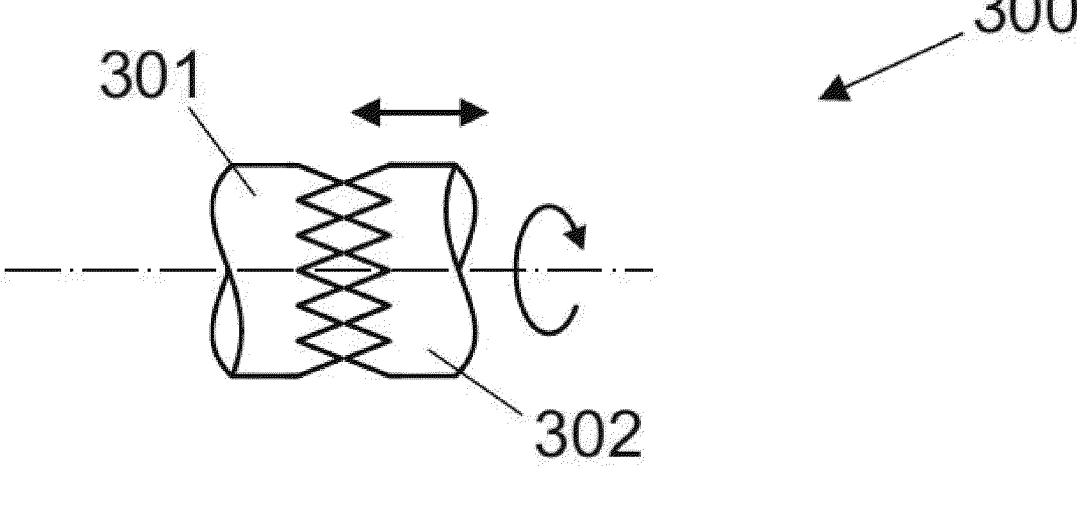
FIG. 4 shows a cross section view of the dosage counting mechanism of FIG. 3.

Rotation of the follower part 302 disengages the profiled section of the cam part 301 from the profiled section of the follower part 302. The cam part 301 is fixed relative to the follower part 302 and is unable to rotate such that the follower part 302 is pushed axially away from the cam part 301 as it is rotated, as shown in FIG. 4. An 'upslope' section of the sawtooth profile pushes the two parts apart. The spring 303 is compressed as the follower part 302 moves away from the cam part 301. As the follower part 302 rotates further, the cam part 301 and the follower part 302 can move back together. On the 'downslope' section of the sawtooth profile, the two parts can move together. The spring 303 expands and urges the follower part 302 axially towards the cam part 301.

As the follower part 302 continues to rotate relative to the cam part 301, it is caused to move reciprocally in an axial direction. The sawtooth profile of the cam part 301 results in reciprocal motion of the follower part 302. Each 'tooth' on the sawtooth profile may correspond to a minimum value for the dose delivery operation. That is, each tooth may correspond to a click of the dispensing clicker 300 associated with the ejection of the medicament dose. The follower part 302 may reciprocate once for each step decrease in the dosing amount as the dose is delivered during the delivery phase.

Figure 5:
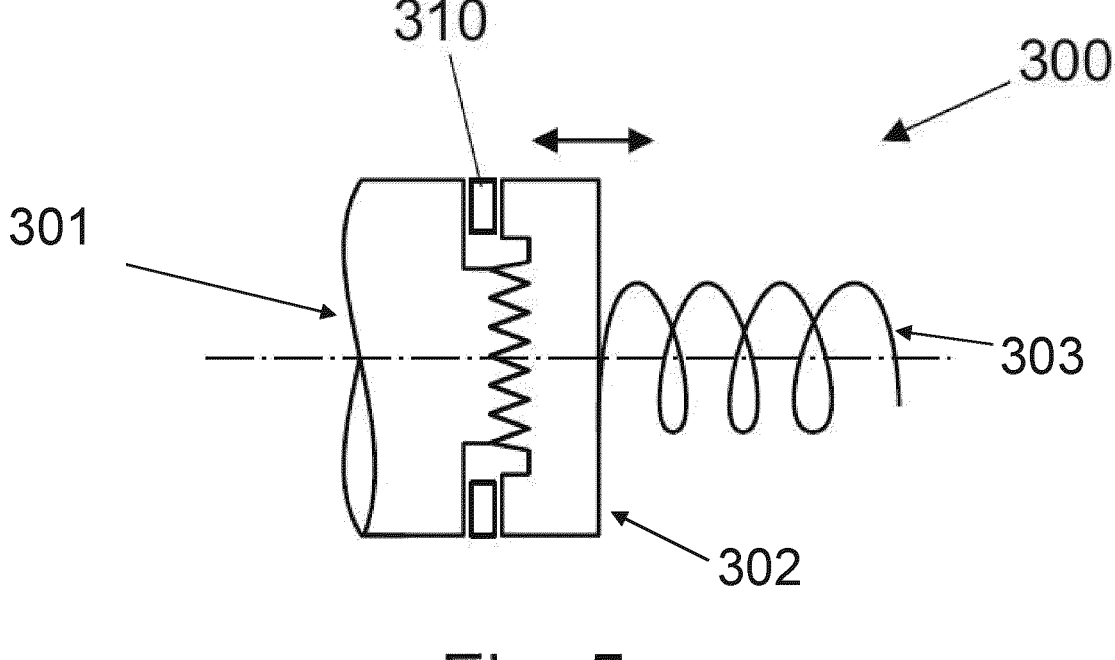
FIG. 5 shows a cross section view of the dosage counting mechanism of FIG. 3.

The dose detection mechanism 300 further comprises a piezo-electric sensor 310. The piezo-electric sensor is an example of a contact sensor. As shown in FIG. 5, the dose detection mechanism 300 may comprise an outer section, arranged radially outside the inner section shown in FIGS. 3 and 4. The piezo-electric sensor 310 may be arranged in the outer section of the dose detection mechanism 300. The piezo-electric sensor 310 may be formed as a piezo ring which extends the outer circumference of the inner section.

In some other examples, the piezo-electric sensor 310 may be formed such that it does not form a complete ring. For instance, the piezo-electric sensor 310 may be formed in a different shape (e.g. square or rectangular) which extends around only a portion of the outer circumference of the inner section of the cam part 301, as for instance, shown in FIG. 7. In such examples, at least one dome may also be formed on the outer section of the dose detection mechanism 300, arranged to extend around at least a portion of the outer circumference of the inner section of the cam part 301. In this way, the dome(s) may ensure that the follower part 302 makes proper contact with the piezo-electric sensor 310 and/or that the follower part 302 is prevented from tilting when the follower part 302 comes together with the cam part 301.

In an embodiment, the piezo-electric sensor 310 is attached to the cam part 301. The piezo-electric sensor 310 is arranged to make contact with the follower part 302. The follower part 302 may be pushed against the piezo-electric sensor 310 by the spring 303. Alternatively, the piezo-electric sensor 310 may be attached to the follower part 302. The piezo-electric sensor 310 may be arranged to make contact with the cam part 301. The piezo-electric sensor 310 may be pushed against the cam part 301 by the spring 303.

The piezo-electric sensor 310 is arranged such that the follower part 302 is in contact with the piezo-electric sensor 310 when the profiled sections of the cam part 301 and the follower part 302 are fully engaged. As the profiled section of the cam part 301 disengages from the profiled section of the follower part 302, the follower part 302 is separated from the piezo-electric sensor 310. In this way, the reciprocal motion of the follower part 302 causes the follower part 302 to repeatedly separate and then make contact with the piezo-electric sensor 310.

The piezo-electric sensor 310 is configured to generate an electric voltage in response to an applied pressure. The piezo-electric sensor 310 generates the electric voltage in response to physical contact with another element. For example, piezo-electric sensor 310 in response to physical contact with the follower part 302. The piezo-electric sensor 310 provides a sensor signal having a voltage level which is indicative of physical contact between the piezo-electric sensor 310 and the follower part 302. The sensor signal has a high voltage level when the piezo-electric sensor 310 is in contact with the follower part 302. In this way, the piezo-electric sensor 310 may produce the sensor signal with a voltage signal corresponding to the reciprocal motion of the follower part 302.

Each rotation of the follower part 302 as the dose is delivered corresponds to one tooth on the sawtooth profile and results in a corresponding voltage peak in the sensor signal. Thus each step decrease in the dosage amount as the dose is delivered during the delivery phase results in a corresponding voltage peak in the sensor signal.

The sensor signal output by the piezo-electric sensor 310 is provided to an electronics system. The electronics system comprises a signal filter, an analogue-to-digital converter (ADC), a processor, a battery, and a display. The signal filter is configured to filter the sensor signal for improved processing by the ADC and the processor. The signal filter may comprise a low pass filter configured to reduce high frequency noise in the sensor signal. The signal filter may comprise a threshold filter configured to reduce low-level noise in the sensor signal.

The ADC is configured to convert the analogue sensor signal into a digital signal for processing. The ADC may convert each voltage peak generated by contact between the piezo-electric sensor 310 and the follower part 302 to a logic high, or digital "1". Otherwise, sections of the sensor signal not comprising a voltage peak may be converted to a logic low, or digital "0".

In some examples, the battery may be co-located with the processor of the electronics system. In other examples, the battery may be co-located with the piezo-electric sensor 310.

The electronics system may further comprise an amplifier circuit. The amplifier circuit may amplify the voltage pulses generated by the piezo-electric sensor 310 as required for further processing.

In some examples, the processor may comprise a microcontroller. The processor may include an input pin which receives sensor signal from the piezo-electric sensor 310. The processor input pin may be configured to trigger an interrupt in the processor in response to receiving the sensor signal such that the processor can count voltage pulses associated with a dosage delivery provided in the sensor signal. The processor may receive sensor signals directly from the piezo-electric sensor 310, or may receive the sensor signals via the signal filter, the ADC and/or the amplifier circuit.

In some examples, the processor may distinguish voltage pulses in the received sensor signal associated with a dosage delivery and voltage pulses in the received sensor signal associated with external stimulus, for example, dropping of the injection device. For instance, the processor may implement signal analysis algorithms to determine differences in signal characteristics.

In some other examples, the received sensor signal may be used to "wake up" the processor. The processor may be configured to be in a sleep mode in order to preserve energy expenditure and thus battery power until it is caused to transition into an active mode. For example, in response to a first "click" associated with a dosage delivery being detected in the sensor signal, the processor may be configured to transition from the sleep mode into the active mode.

The processor is configured to count the number of voltage peaks in the sensor signal. Based on the number of voltage peaks, the processor may determine a corresponding value for the dosage amount delivered. The processor may output the determined dosage amount delivered for display on the display. Each voltage peak in the sensor signal may result in a corresponding increase in the determined dosage amount delivered. The determined dosage amount delivered may be increased by a predetermined amount, based on a minimum dosage delivery increment of the injection device. Each 'click' of the dispensing clicker 300 associated with the medicament dose may result in a corresponding increase in the determined dosage amount delivered.

The processor may be configured to store the currently display dosage amount in the memory. The processor may store the dosage amount along with a current time and/or date.

The injection device may further comprise a communications module in order to transmit the stored data to an external device. For instance, the communications module may provide wireless communications capabilities (e.g. Bluetooth, Wi-Fi, NFC) or wired communications capabilities. The external device may be any external device suitably for receiving the transmitted data, for instance, a smartphone, a personal computer, a server, or another smart device.

Figure 6:
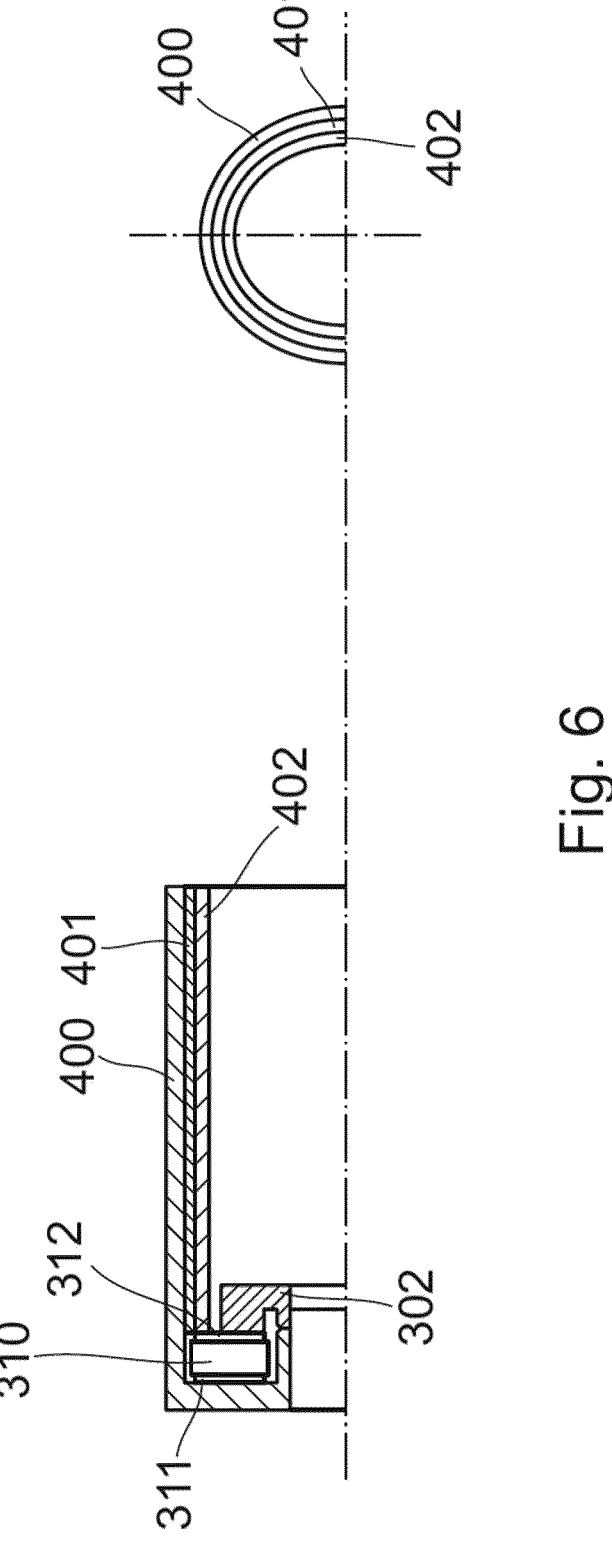
FIG. 6 shows a cross section view of the dosage counting mechanism of FIG. 3.

FIG. 6 shows an arrangement for connecting the piezoelectric sensor 310 with the electronics system. The electronics system, and the connections thereof as shown in FIG. 6, may be arranged in the housing 210 of the injection device 200. The electronics system and the connections thereof are therefore arranged to be fixed, relative to the piezo-electric sensor 310. The piezo-electric sensor 310 may be electrically connected with the electronic system through contacts, for instance tracks or wires. In some other examples, the electronics system may be arranged between the housing 210 and the cartridge holder 222.

The contacts are provided by an inner sleeve 402 and an outer sleeve 400. For example, a first contact is provided by the inner sleeve 402 and a second contact is provided by the outer sleeve 400. The inner sleeve 402 is separated from the outer sleeve 400 by an insulation sleeve 401. The piezo-electric sensor 310 comprises a first conductive surface 311 and a second conductive surface 312. The inner sleeve 402 is configured to make electrical contact with the first conductive surface 312 of the piezo-electric sensor 310, and the outer sleeve 400 is configured to make electrical contact with the second conductive surface 311. In this way, transmission of electronic signals between the electronics system and the piezo-electric sensor 310 can be performed via the electrical connections. Additionally or alternatively, the electronics system can provide power to the piezo-electric sensor 310 via the electrical connections.

As described above, reciprocal motion of the follower part 302 for each step decrease in the dosing amount as the dose is delivered causes the follower part 302 to repeatedly separate and then make contact with the piezo-electric sensor 310. Thus according to the above described arrangement, electrical contact between the electronics system and the piezo-electric sensor 310 can be maintained during dosage delivery.

Figure 7:
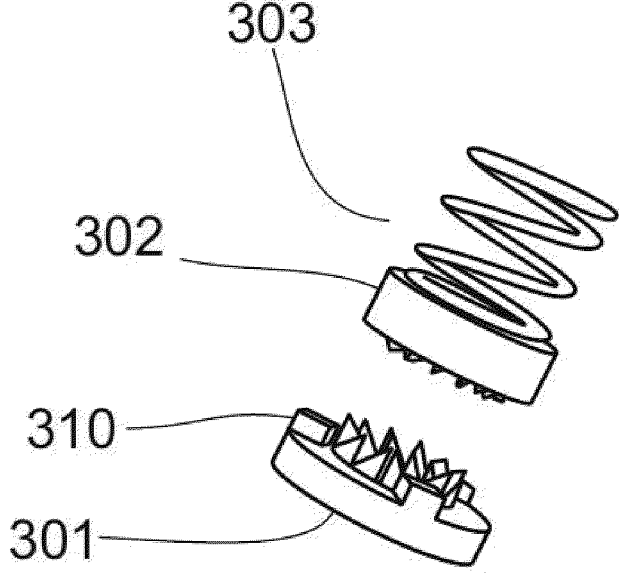
FIG. 7 shows a view of an alternative dosage counting mechanism.

FIG. 7 shows a view of an alternative dosage counting mechanism. In this example, the piezo-electric sensor 310 is formed in a rectangular shape which extends around only a portion of the outer circumference of the inner part of the cam part 301. In addition to the piezo-electric sensor 310, the cam part 301, as shown in FIG. 7, may include at least one dome which extends around a portion of the outer circumference of the inner part of the cam part 301, wherein the portion which the domes extend around may be different, and/or set apart from the portion which the piezo-electric sensor 310 extends around.

Although claims have been formulated in this application to particular combinations of features, it should be understood that the scope of the disclosure also includes any novel features or any novel combinations of features disclosed herein either explicitly or implicitly or any generalisation thereof, whether or not it relates to the same features as presently claimed in any claim and whether or not it mitigates any or all of the same technical problems as does the present disclosure. The applicant hereby gives notice that new claims may be formulated to such features and/or combinations of features during the prosecution of the present application or of any further application derived therefrom.

Although several embodiments have been shown and described, it would be appreciated by those skilled in the art that changes may be made in these embodiments without departing from the principles of the present disclosure, the scope of which is defined in the claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. An apparatus for detecting a manipulation of an injection device, the apparatus comprising:
   a cam part that is configured to be rotatable relative to a follower part;
   a resilient member arranged to urge the cam part and the follower part towards abutment with each other, wherein rotation of the cam part relative to the follower part causes a reciprocating motion of the follower part; and
   a contact sensor provided between the cam part and the follower part and configured to detect the reciprocating motion of the follower part.

2. The apparatus of claim 1, wherein the follower part is configured to move reciprocally in an axial direction of the injection device.

3. The apparatus of claim 1, wherein the cam part comprises:
   a profiled section comprising an axially varying profile arranged to be in abutment with the follower part and configured to cause the reciprocating motion of the follower part, and
   a flat section with a lower axial variation than the profiled section and configured to separate from the follower part upon the reciprocating motion of the follower part.

4. The apparatus of claim 1, wherein the apparatus is configured to be arranged within a housing of an injection device, wherein the follower part is configured to move reciprocally in an axial direction of the injection device, wherein the cam part comprises a profiled section comprising an axially varying profile arranged to be in abutment with the follower part and configured to cause the reciprocating motion of the follower part, and wherein the contact sensor is arranged on the cam part and is configured to separate from the follower part upon the reciprocating motion of the follower part.

5. The apparatus of claim 4, wherein the cam part comprises
   a flat section with a lower axial variation than the profiled section and configured to separate from the follower part upon the reciprocating motion of the follower part.

6. The apparatus of claim 1, wherein the cam part is rotationally fixed and the follower part is rotatable.

7. The apparatus of claim 6, wherein the follower part is configured to rotate in response to the injection device delivering a dosage amount.

8. The apparatus of claim 1, wherein rotation of the cam part is configured to set a dosage amount for the injection device.

9. The apparatus of claim 1, wherein the apparatus further comprises a dosage setting mechanism configured to be rotatable to set a dosage amount for the injection device.

10. The apparatus of claim 1, wherein the cam part comprises:
    a profiled section comprising an axially varying profile arranged to be in abutment with the follower part and configured to cause the reciprocating motion of the follower part, and
    a flat section with a lower axial variation than the profiled section and configured to separate from the follower part upon the reciprocating motion of the follower part.

11. The apparatus of claim 10, wherein the flat section and the profiled section of the cam part are spaced apart radially.

12. The apparatus of claim 10, wherein the follower part comprises a profiled section corresponding to the profiled section of the cam part.

13. The apparatus of claim 10, wherein the profiled section comprises a sawtooth profile.

14. The apparatus of claim 13, wherein the sawtooth profile comprises a plurality of teeth, each tooth of the plurality of teeth corresponding to a fixed dosage amount for the injection device.

15. The apparatus of claim 10, wherein the contact sensor is arranged on the flat section of the cam part.

16. The apparatus of claim 1, wherein the contact sensor is arranged on a section of the follower part adjacent to the cam part.

17. The apparatus of claim 1, wherein the contact sensor is a piezo-electric contact sensor configured to generate an electric current on contact with another part of the injection device.

18. The apparatus of claim 1, wherein the apparatus includes a cartridge containing medicament.

19. The apparatus of claim 7, wherein an amount of rotation of the follower part corresponds to the dosage amount.

20. The apparatus of claim 9, wherein the follower part is fixed in position in relation to the dosage setting dial.

\* \* \* \* \*